US012633423B2

(12) United States Patent
Odaibo

(10) Patent No.: US 12,633,423 B2
(45) Date of Patent: May 19, 2026

(54) RETRIEVAL-AUGMENTED FUSION LANGUAGE MODELS FOR AI-BASED PROTEIN AND DRUG DESIGN

(71) Applicant: Stephen Gbejule Odaibo, Sugar Land, TX (US)

(72) Inventor: Stephen Gbejule Odaibo, Sugar Land, TX (US)

(73) Assignee: Deep EigenMatics, Inc., Sugar Land, TX (US)

( * ) Notice: Subject to any disclaimer, the term of this patent is extended or adjusted under 35 U.S.C. 154(b) by 0 days.

(21) Appl. No.: 19/218,291

(22) Filed: May 25, 2025

(65) Prior Publication Data

US 2025/0285773 A1 Sep. 11, 2025

(51) Int. Cl.
*G16H 70/40* (2018.01)
*G06N 3/12* (2023.01)

(52) U.S. Cl.
CPC .............. *G16H 70/40* (2018.01); *G06N 3/12* (2013.01)

(58) Field of Classification Search
CPC ................................. G16H 70/40; G06N 3/12
See application file for complete search history.

(56) References Cited

PUBLICATIONS

Gao et al., "The Synthesizability of Molecules Proposed by Generative Models", J. Chem. Inf. Model. (2020) vol. 60, pp. 5714-5723. (Year: 2020).*

* cited by examiner

*Primary Examiner* — Jerry Lin

(57) ABSTRACT

Methods and apparatus for obtaining representations of proteins and small molecule drugs for synthesis; wherein input queries into trained mixed modality protein and natural language models are augmented with relevant query-related documents. In one embodiment, the relevant query-related documents are obtained by maximum inner product search of an embedding latent vector space into which the query and the documents are projected. The top-k most relevant documents to the query are then combined with the query as input into the trained mixed modality language model. In one embodiment, the mixed modality model is an autoregressive multicapitate transformer whose decoder output heads correspond to the represented modalities. The method returns mixed modality output representations of proteins or small molecule drugs for synthesis or manufacture.

11 Claims, 10 Drawing Sheets

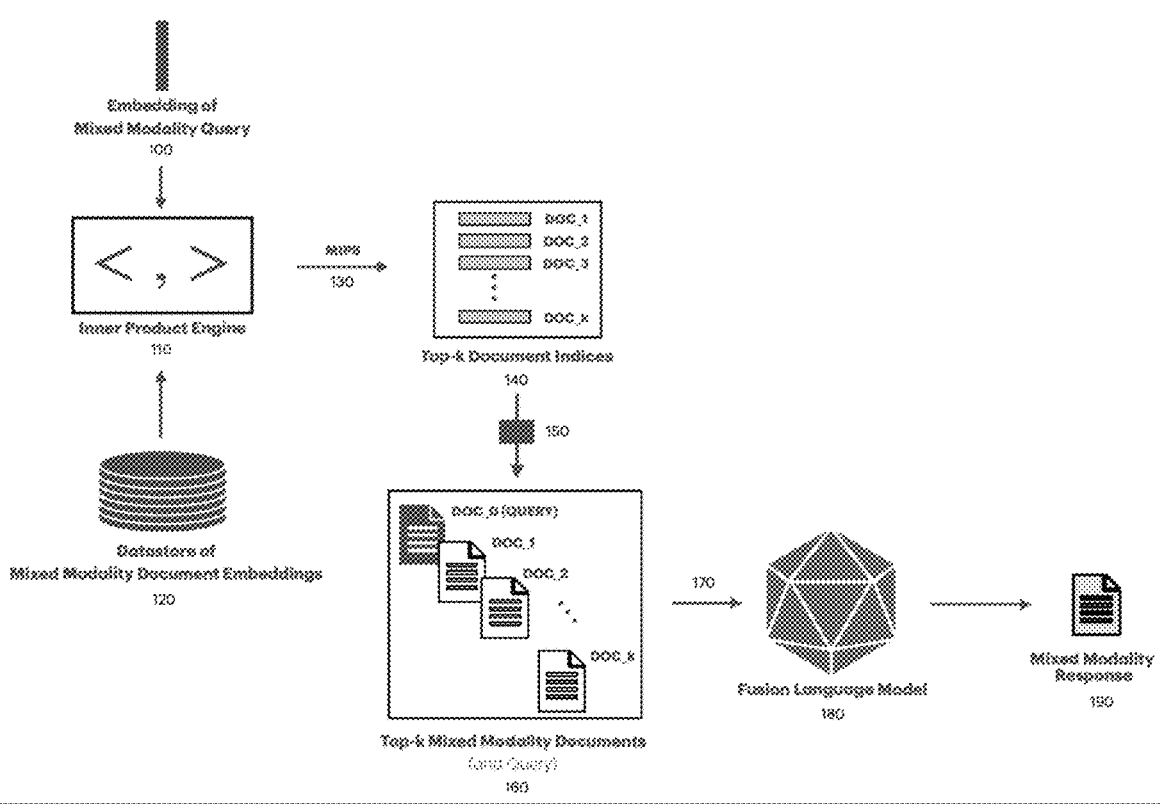
FIG. 1 Illustrative Overview of Retrieval Augmented Generation by a Mixed Modality Language Model.

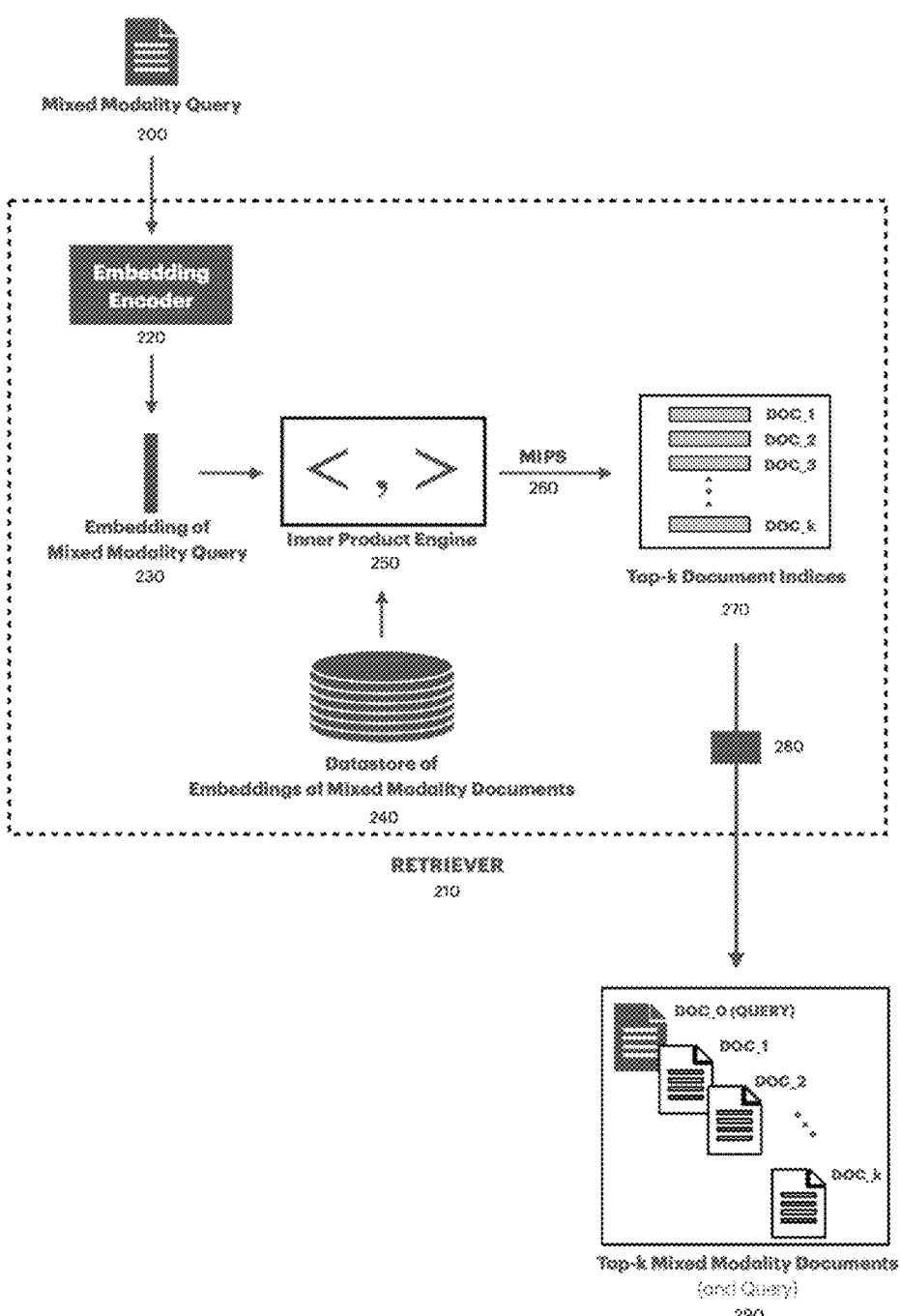
FIG. 2 Illustrative Example of a Retriever Module in Retrieval Augmented Generation.

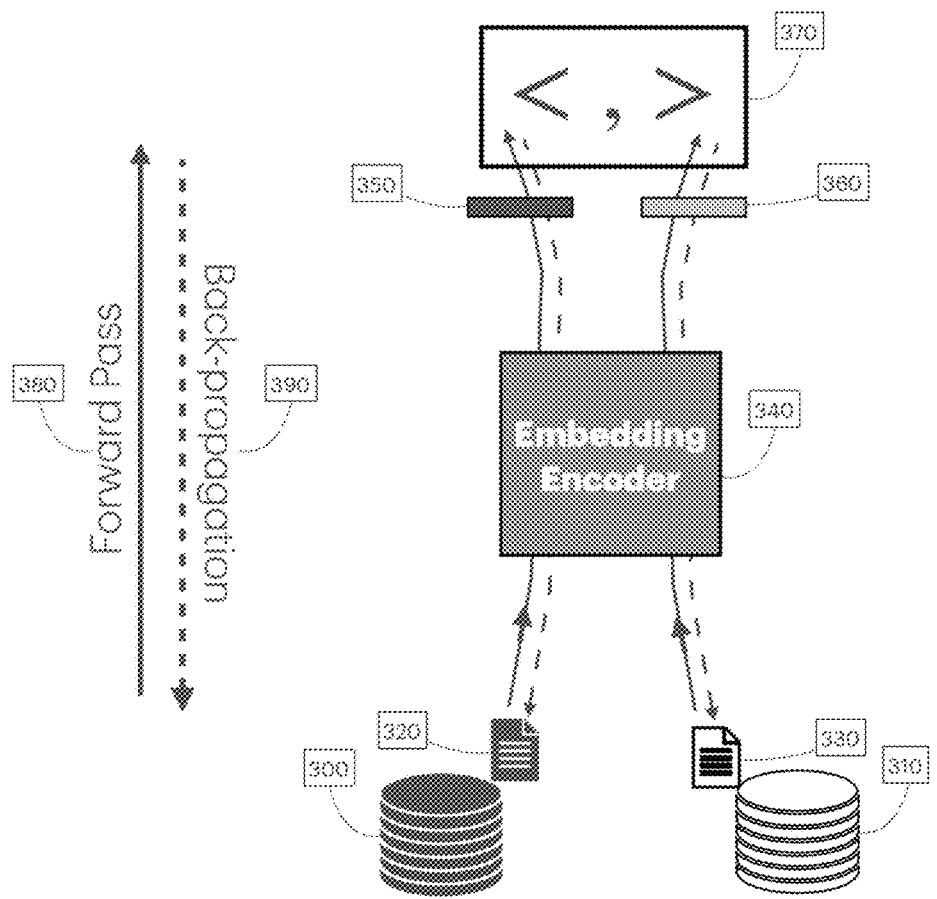
FIG. 3 Illustrative Example of a Training Process of an Embedding Encoder for Retrieval Augmented Generation.

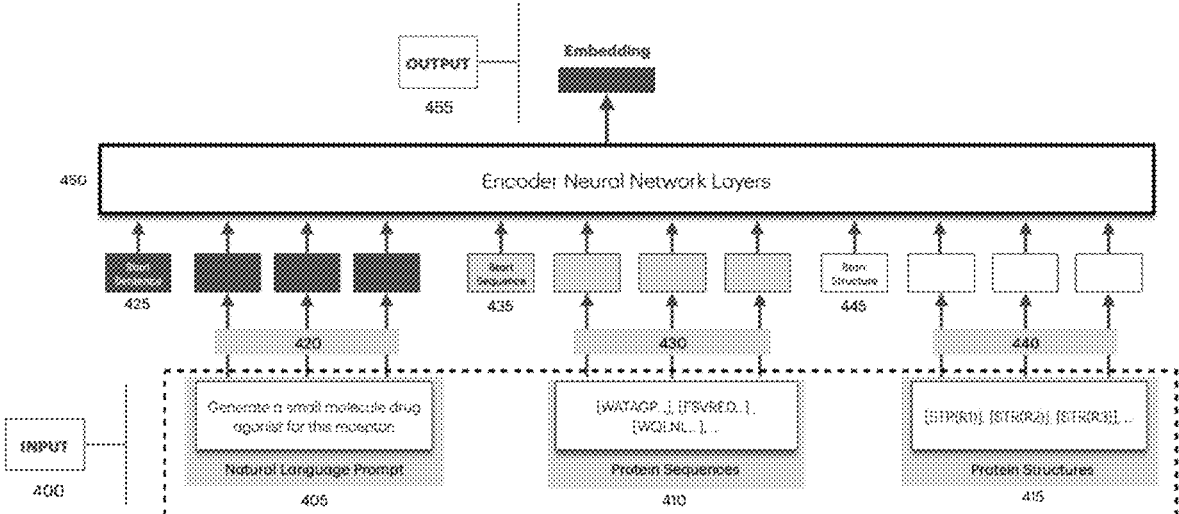
FIG. 4 Illustrative Example of Inference with an Embedding Encoder in Mixed Modality
Retrieval Augmented Generation.

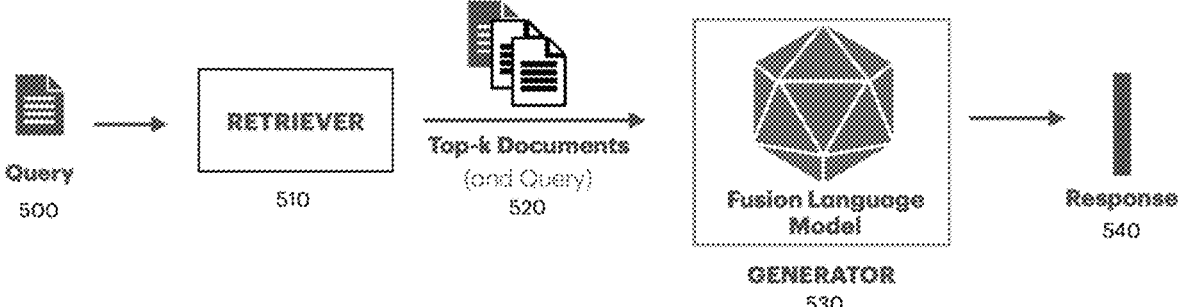
FIG. 5 Illustrative Overview of Inference in a Retrieval Augmented Fusion Language Model.

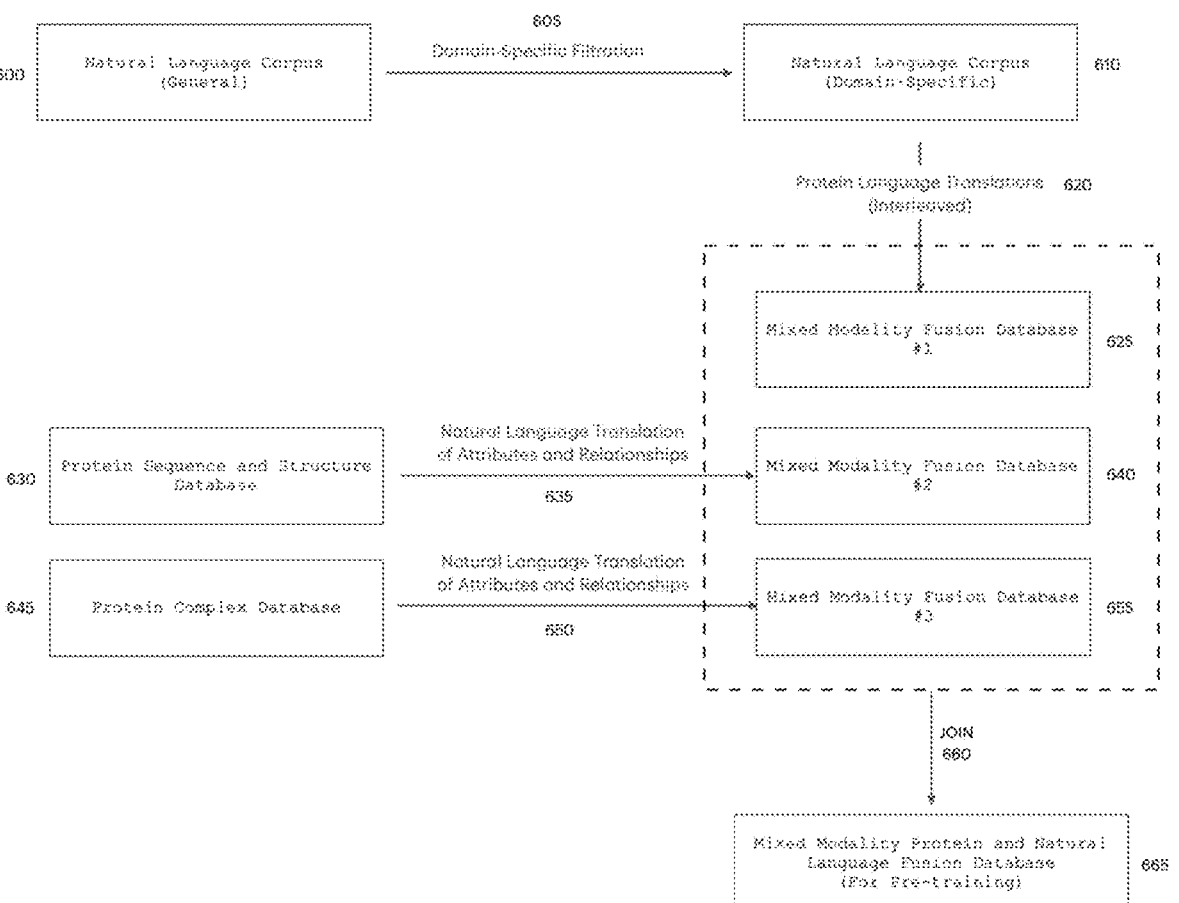
FIG. 6 A Schematic Flow Diagram of an Example of Database Crossing to Yield a Mixed Modality Protein and Natural Language Fusion Database.

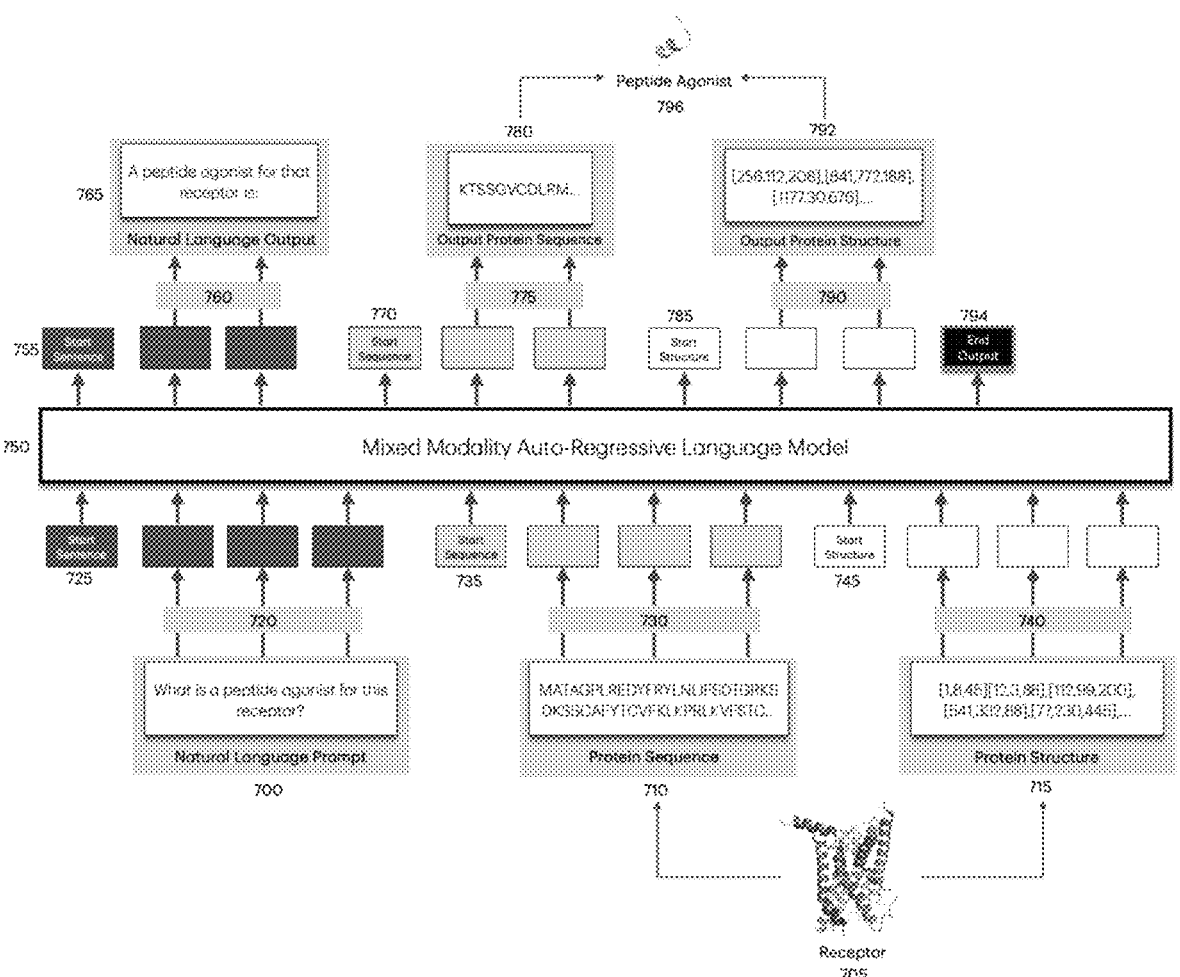
FIG. 7 Illustrative Overview of Inference with a Mixed-Modal Early-Fusion Language Model for Protein and Drug Design.

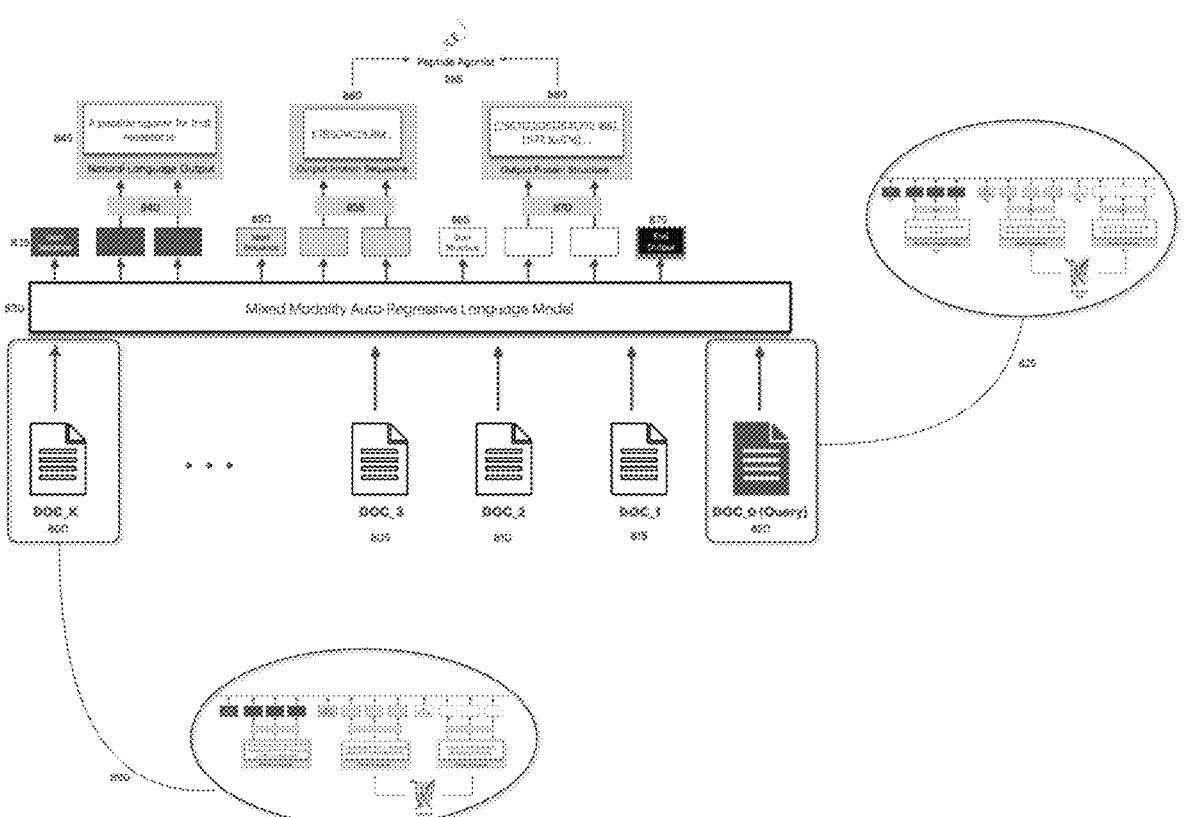
FIG. 8 Illustrative Example of In-Context Augmentation with Retrieved Documents in a
Mixed Modality Protein and Natural Language Model.

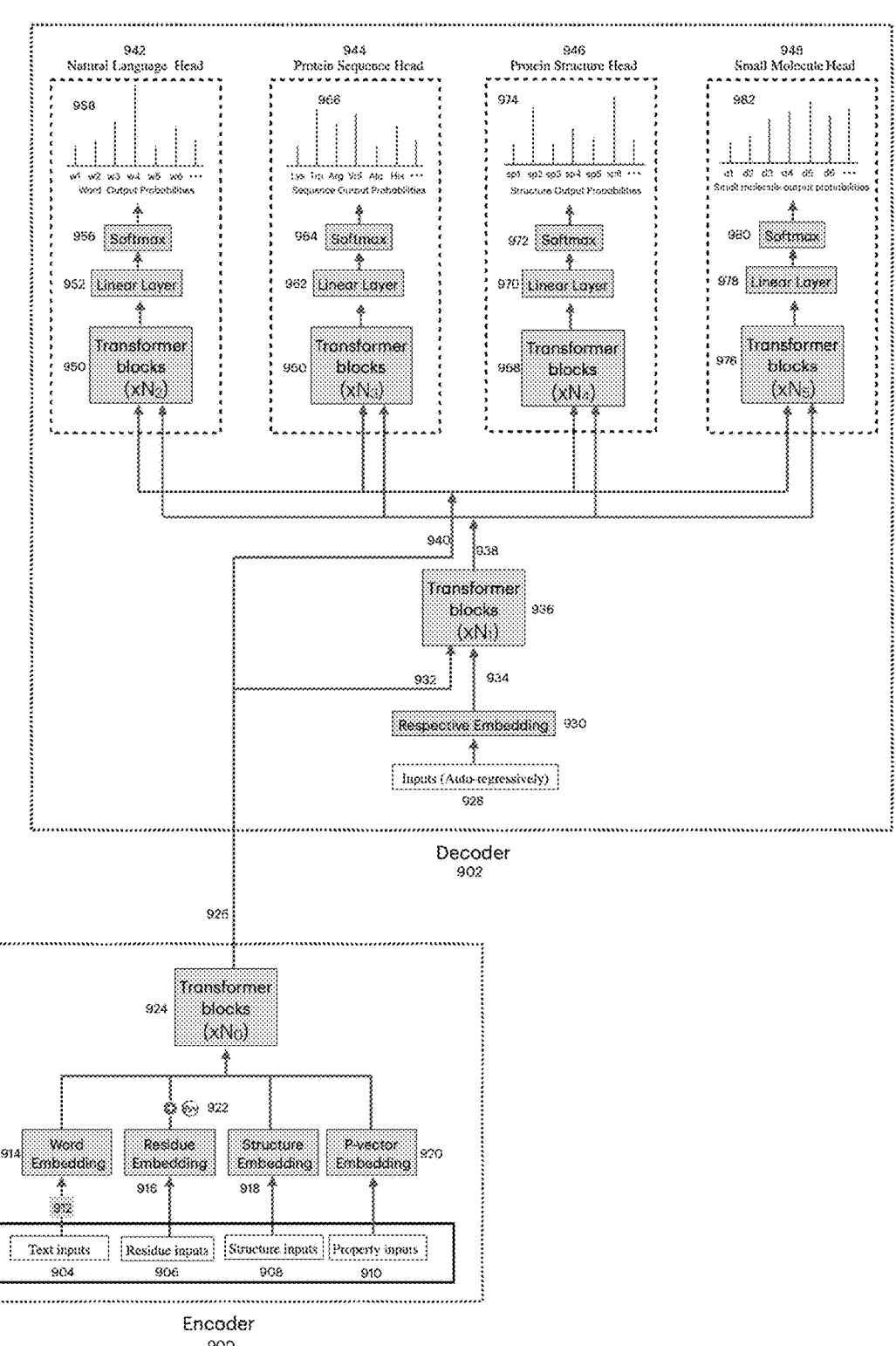
FIG. 9 A Multicapitate Encoder-Decoder Transformer Inference Architecture for Mixed Modality Protein and Natural Language Fusion.

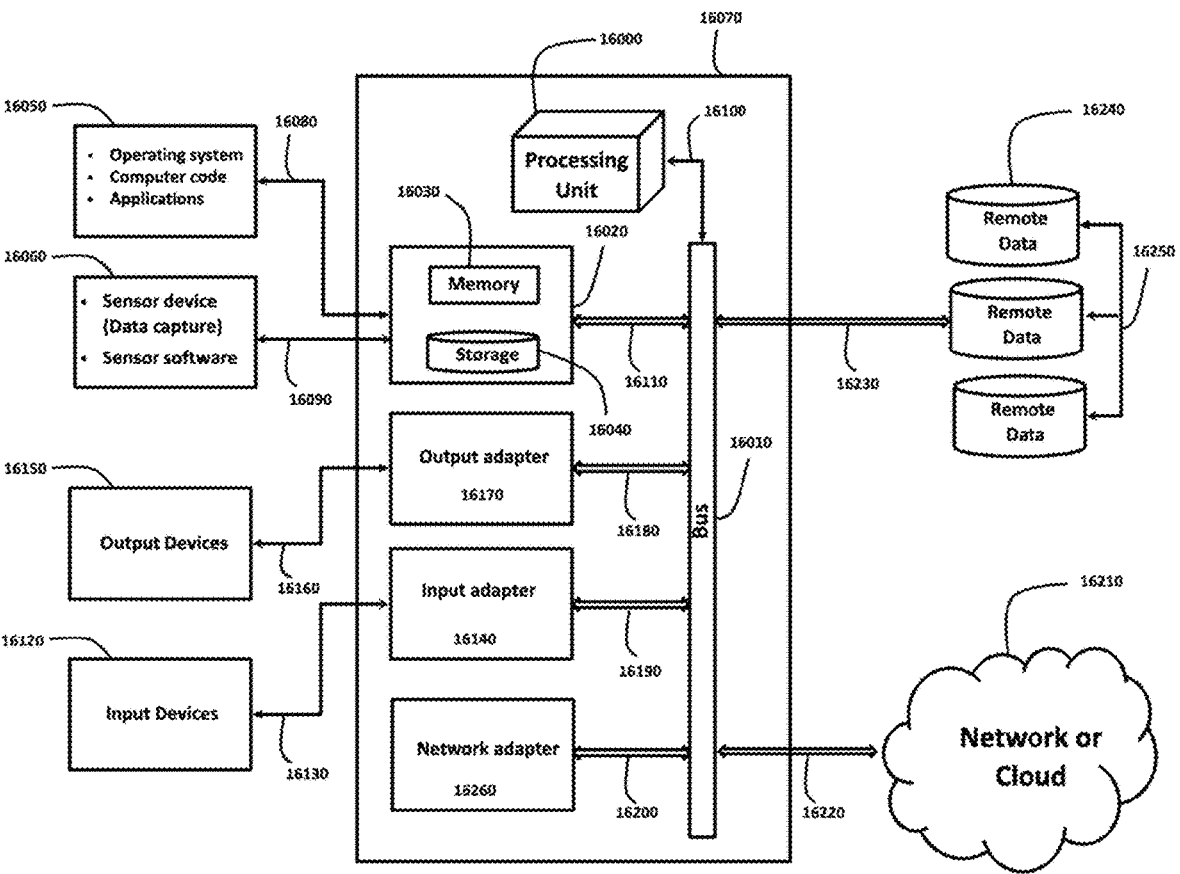
FIG. 10 Computing Environment

RETRIEVAL-AUGMENTED FUSION LANGUAGE MODELS FOR AI-BASED PROTEIN AND DRUG DESIGN

FIELD OF THE INVENTION

The present invention relates generally to Artificial Intelligence (AI) and Machine Learning (ML) methods for protein and drug ligand design and structure determination, and specifically to large language models for protein and drug design.

BACKGROUND OF THE INVENTION

Currently, many diseases are without an effective treatment or without any treatment at all. This is largely because the research and development pipeline for new drugs is tremendously expensive and lengthy, often costing over $2 billion and more than 10 years to get a single candidate drug through clinical testing phases. Yet despite the exorbitant investment of time and resources, a high percentage of drugs fail in the clinical testing phases.

Deep learning techniques applied towards protein and drug design have generated much interest in the last few years. This is because deep learning has the potential to enhance and accelerate the drug discovery and development pipeline. For instance, large language models, the vast majority of which are transformer-based architectures, have been widely applied towards protein sequence and structure determination problems.

For the transformer architecture, see:

Vaswani, A., Shazeer, N., Parmar, N., Uszkoreit, J., Jones, L., Gomez, A. N., Kaiser, Ł. and Polosukhin, I., 2017. Attention is all you need. *Advances in Neural Information Processing Systems*, 30.

The transformer solved a long context memory deficit problem in neural machine translation wherein, during translation of a sequential stream, the algorithm forgets the aspects of the context from earlier in the stream. Hence neural machine translation was challenging especially for long context cases. Transformer addressed this problem via a parallelizable version of the attention mechanism. This enabled the translation algorithm to learn what to attend to within the context while translating any given token in the stream. Furthermore, its learning of how to distribute its attention is done in an end-to-end differentiable way.

Transformer-architectures have found several direct applications within protein sequence and structure determination, and algorithms such as alphafold leveraged transformers significantly-see:

Jumper, J., Evans, R., Pritzel, A., Green, T., Figurnov, M., Ronneberger, O., Tunyasuvunakool, K., Bates, R., Židek, A., Potapenko, A. and Bridgland, A., 2021. Highly accurate protein structure prediction with AlphaFold. *Nature*, 596(7873), pp. 583-589.

One problem with standard transformer-like and other large language model architectures, however, is that foundational models require a vast amount of data, computational processing power, time, and cost to develop. Furthermore, once developed, the weights are frozen and therefore cannot readily account for new information that was not part of the original training dataset.

Another significant problem is that standard large language models are typically unimodal, typically of the natural language modality alone, and therefore are not well-suited for problems in protein and drug design, where multiple representation modalities are typically required to properly represent proteins and their features.

Conversely, most existing protein language models are also typically unimodal of the protein sequence modality. Furthermore, the few existing multimodal protein language models are typically of protein sequence and structure modalities alone, without a natural language modality. This is a significant problem because much of what is known about proteins and their features today are represented in natural language modality. Therefore, to adequately represent proteins and their features, not only are multi modal language models required, but more specifically, multimodal language models that at least include both natural language as well as protein sequence modalities are required.

Retrieval augmented generation is a method that augments large language model input queries with related documents from a datastore, thereby becoming able to access non-parametric information—i.e. via a document datastore, the model gets access to information not encoded in the weights of the language model during training. In particular, the datastore can be readily updated at low cost as new information becomes available, and the language model is able to use such non-parametric information in-context without needing to update the weights of the language model itself. In other words, the information source can be augmented and updated without needing to spend the great amount of time and computational cost required to retrain or fine-tune the model.

Retrieval augmented generation was introduced to the field of large language models in general in the year 2020, see:

Guu, K., Lee, K., Tung, Z., Pasupat, P. and Chang, M., 2020 November. Retrieval augmented language model pre-training. In *International Conference on Machine Learning* (pp. 3929-3938). PMLR., and see:

Lewis, P., Perez, E., Piktus, A., Petroni, F., Karpukhin, V., Goyal, N., Küttler, H., Lewis, M., Yih, W. T., Rocktäschel, T. and Riedel, S., 2020. Retrieval-augmented generation for knowledge-intensive nip tasks. *Advances in Neural Information Processing Systems*, 33, pp. 9459-9474.

There have been a number of instances where retrieval augmented generation techniques were applied to protein language models. For instance, see:

Mahbub, S., Kundu, S. and Xing, E. P., PRISM: Enhancing Protein Inverse Folding through Fine-Grained Retrieval on Structure-Sequence Multimodal Representations. In ICLR 2025 Workshop on Machine Learning Multiscale Processes.

However, as noted, mixed modality models including at least a natural language modality, a protein sequence modality, and a protein structure modality are necessary for adequate representation of proteins and their features; yet there were no such methods in existence prior to the disclosure of this invention.

Prior to the disclosure of this invention, there were no retrieval augmented methods available for mixed modality protein and natural language models.

Prior to the disclosure of this invention, there were no retrieval augmented methods in existence for mixed modality language models wherein the modalities included natural language and protein sequence.

And prior to the disclosure of this invention, there were no retrieval augmented methods in existence for mixed modality language models wherein the modalities include natural language, protein sequence, and protein structure.

Therefore, this invention addresses a significant unmet need for retrieval-augmented mixed modality protein and natural language models. By doing so, it provides a method with a high likelihood to accelerate the drug discovery and development pipeline and yield novel and effective treatments to many diseases.

OBJECTS OF THE INVENTION

It is an object of this invention to provide a system, method, and apparatus using protein and natural language fusion models to obtain representations of proteins and drug ligands to manufacture, wherein the method can access new information without needing to update the weights of the base model.

Another object of this invention is to provide a system, method, and apparatus using protein and natural language fusion models to obtain representations of proteins and drug ligands to manufacture, wherein the method can access new information without needing to update the weights of the base model and without needing to change the inference procedure from the user's perspective.

Yet other objects, advantages, and applications of the invention will be apparent from the specifications and drawings included herein.

SUMMARY OF THE INVENTION

The invention disclosed herein includes a method comprising receiving, at a processor, a trained mixed modality protein and natural language model. In addition, a retriever module (or retriever function) is used, wherein given an input query for the trained mixed modality model, the retriever module outputs a set of documents related to the input query. The input query and its associated set of related documents are then passed into the trained mixed modality protein and natural language model for inference. Per the input query request, the trained mixed modality model outputs representations of proteins and ligand drugs for manufacture.

Here and in the claims, the terms retriever module and retriever function will be used interchangeably, and have the same meaning described here in the specifications.

In some embodiments of the invention, after the relevance of each document to the input query is determined, the documents are then ranked by relevance, and then the top-k documents are returned as output of the retriever module; where k is a hyperparameter of the system.

The top-k documents along with the input query are then passed as input into the trained mixed modality protein and natural language model for inference. The model then returns the response as output.

In some embodiments of the invention, the retriever module consists of an embedding encoder; a datastore of document embeddings; and an algorithm to assess relevance of documents to queries via their embeddings and to rank them accordingly.

The embedding encoder serves to project the query and each of the documents into a latent vector space within which relevance of each document to any given input query can be determined. In one embodiment, the embedding encoder is a neural network trained on an objective wherein the inner product is proportional to the relevance of documents to each other. In other words, the more related two documents are, the higher the inner product of their embeddings, and the less related they are, the lower the inner product of their embeddings. In particular, considering that any given query is itself a document, the relevance of documents in the datastore to the query is encoded by the inner product of the query embedding to the document's embedding.

The embedding encoder is used to transform the documents in a database, and this only needs to be done once for each database. The resulting datastore of document embedding vectors is then available for use during the retrieval process.

On the other hand, the mixed modality queries are essentially arbitrary and are not pre-known ahead of inference time. Hence, at inference time, each mixed modality query first needs to be transformed into a vector embedding using the embedding encoder. Here and in the claims, by mixed modality query (or output) we mean that the query (or output) representation consists of one or more of the specified modalities. By way of example and not limitation, depending on the particular mixed modality model, the modalities may include natural language modality, protein sequence modality, protein structure modality, small molecule drug modality, pre-specified property format ("p-vector") modality, or more.

Of the embodiments of the invention utilizing an inner product objective, by way of non-limiting example, some further utilize a Maximum Inner Product Search (MIPS) algorithm to perform and rank the inner products of a given query with the documents in a datastore. This yields a top-k documents output by relevance, wherein k is a hyperparameter of the system. Specifically, the MIPS yields a ranking of document indices from which the associated top-k documents are obtained via look-up procedure.

By way of example not limitation, the embedding encoder may be BM25, Latent Semantic Indexing (LSI), a bi-encoder, a cross-encoder, or hybrids such as colBERT which use bi-encoders for initial retrieval and then cross-encoders for re-ranking.

The input query and its top-k related documents are passed as a combined input into the mixed modality protein and natural language model. In some embodiments, the query and related documents are simply concatenated, resulting, in effect, in a longer input which is processed in the same way at inference.

By way of example and not limitation, the mixed modality protein and natural language model may be a transformer. In such instances of fixed context length, the concatenated input only implies shorter length of zero padding of the context due to the longer input. However, the general form of the input is otherwise unchanged. Therefore, following retrieval and the subsequent formation of a combined input consisting of the query and its related documents, all aspects of the inference process proceed the same as in the standard (i.e. non-retrieval-augmented) case.

In summary, the invention disclosed herein consists of systems, methods, and apparatus to use non-parametric memory datastore to augment the parametric knowledge available through trained mixed modality protein and natural language models; wherein the method uses mixed modality input queries specified to yield outputs that are representations of proteins and ligand drugs to manufacture.

The invention consists of several outlined processes below, and their relation to each other, as well as all modifications which leave the spirit of the invention invariant. The scope of the invention is outlined in the claims section.

BRIEF DESCRIPTION OF THE DRAWINGS

In the following detailed description of the invention, we reference the herein listed drawings and their associated descriptions, in which:

FIG. 1 is an illustrative overview of retrieval augmented generation by a mixed modality language model.

FIG. 2 is an illustrative example of a retriever module in retrieval augmented generation.

FIG. 3 is an illustrative example of a training process of an embedding encoder for retrieval augmented generation.

FIG. 4 is an illustrative example of inference with an embedding encoder in mixed modality retrieval augmented generation.

FIG. 5 is an illustrative overview of inference in a retrieval augmented fusion language model.

FIG. 6 is a schematic flow diagram of an example of database crossing to yield a mixed modality protein and natural language fusion database.

FIG. 7 is an illustrative overview of inference with a mixed-modal early-fusion language model for protein and drug design.

FIG. 8 is an illustrative example of in-context augmentation with retrieved documents in a mixed modality protein and natural language model.

FIG. 9 is a multicapitate encoder-decoder transformer inference architecture for mixed modality protein and natural language fusion.

FIG. 10 is an example of a computing environment.

DETAILED DESCRIPTION OF THE PREFERRED EMBODIMENTS

The illustration in FIG. 1 is an overview of an embodiment of retrieval augmented generation by a mixed modality language model. An embedding of a mixed modality query 100 as well as embeddings of mixed modality documents 120 are acted on by inner product operation 110. Specifically, the inner product of the embedding of the mixed modality query is taken with each of the respective mixed modality document embeddings in the datastore 120. The resulting set of inner products is ranked using maximum inner product search (MIPS) 130, and the resulting indices of the top-k documents 140 by inner product is returned as output.

The corresponding top-k documents (and the query) 160 are returned via a look-up procedure 150. The top-k mixed modality documents (and the query) 160 are then passed as input into a trained mixed modality protein and natural language model 180 for inference. This in turn yields a mixed modality response 190 to the augmented query.

FIG. 2 illustrates an example of a retriever module 210 in a mixed modality retrieval augmented generation system. In this embodiment, a mixed modality query 200 is passed into the retriever module 210 as input, and a set of top-k query related documents (along with the query itself) 290 are returned as output by the retriever module.

The retriever module 210 includes an embedding encoder 220 which acts on the mixed modality query to transform it into an embedding vector 230. The retriever module 210 also includes a datastore of document embeddings 240, as well as an inner product engine 250. Inner products of the query embedding with each document embedding is taken and ranked per a MIPS procedure 260, yielding the top-k document indices 270. Finally, a look-up procedure 280 mapping the indices to their corresponding documents yields the top-k mixed modality documents (and query) as output 290.

FIG. 3 is an illustrative example of a training process of an embedding encoder for a retrieval augmented mixed modality language model embodiment. In this embodiment, the embedding encoder 340 is a neural network which is trained using a gradient-based optimization method. A mixed modality query database 300 supplies queries 320 and a document database 310 supplies documents 330. The queries and documents are transformed by the embedding encoder neural network in a shared weights sense, yielding corresponding query embeddings 350 and document embeddings 360 respectively.

In this embodiment, relevance of documents 360 to a given query 350 is measured based on similarity as determined by the inner product 370. In particular, the objective is that for a given query, the inner product with documents related to the query should be high while the inner product with documents unrelated to the query should be low.

A loss function is used wherein the loss is proportionally increased for violations of the objective and proportionally decreased for adherence to the objective. Backwards propagation 390 of gradients from the loss is then used to update the weights of the encoder neural network 340. The training proceeds iteratively till termination criteria are met.

FIG. 4 is an illustrative example of inference with an embedding encoder in mixed modality retrieval augmentation. The input 400 may be a mixed modality query or mixed modality document. In this illustration, the input is a query with its parts respectively represented via a natural language modality 405, a protein sequence modality 410, and a protein structure modality 415. The natural language part 405 is passed through a tokenizer and a word embedding 420. A <start-of-sentence> token 425 indicates the start of a natural language stream of word embeddings. The protein sequence modality stream of tokens are each transformed 430 to embedding vectors. A <start-of-sequence> token 435 indicates the start of this protein sequence stream. Also, for this particular query, each token in the protein structure modality stream 415 is transformed to embedding vectors by a structure embedding 440. The start of the corresponding stream of structure embedding vectors is indicated by a <start-of-structure> token 445.

The entire sequence of embedding vectors is passed as input into a set of encoder neural network layers 450, of which the final layer is a densely connected (Fc7) layer whose output is the embedding 455 which will be used in the MIPS procedure to determine the top-k related documents.

FIG. 5 is an illustrative overview of inference in a retrieval augmented fusion language model. A mixed modality query 500 is passed into a retriever module 510, yielding top-k related documents (and the query) 520. The top-k related documents along with the query are then passed as combined input into a trained fusion language model (a generator) 530 which yields an output response 540.

FIG. 6 is a schematic flow diagram of an example of database crossing to yield a mixed modality protein and natural language fusion database. Such mixed modality databases are used for training of the mixed modality language model, as well as for training of the document and query embedding encoder. In this embodiment, the process starts by receiving a natural language corpus 600, wherein the corpus is large, representative, and general. Next, a domain-specific filtration 605 is performed and yields a domain-specific natural language corpus 610. The extent of the domain-specific filtration 605 is a tunable design factor of the system. In some embodiments, the filtration schema includes selecting data units that contain certain search terms.

The domain-specific natural language corpus 610 is then transformed by interleaving it with protein language translations 620, wherein anywhere a specific protein is referenced in the corpus, the sequence representation of that protein as well as its structure representation (if available) are used as replacement for the natural language representation of that protein in the corpus. This translation process 620 results in a mixed modality fusion database 625 consisting of natural language, protein sequence, and protein structure representations. The source of the sequence and structure translations are protein sequence and structure databases 630.

The protein sequence and structure databases 630 are themselves interleaved with natural language translations of their attributes and relationships 635. This translation yields another mixed modality fusion database 640, consisting of natural language, protein sequence, and protein structure representations. In addition, protein complex databases 645 are also interleaved with natural language translations of their attributes and representations 650, also yielding a mixed modality fusion database 655.

The three types of mixed modality databases derived via the above described database crossings are then joined together 660, yielding a larger combined fusion database 665 that can then be used for training of the protein and natural language fusion language model, or for training of the document and query embedding encoder.

FIG. 7 is an illustrative overview of inference in a mixed modality language model component of an embodiment of the invention; wherein an input query consisting of a stream of mixed modality representations of data-including a natural language representation 700, a protein sequence representation 710, and a protein structure representation 715—is transformed into a mixed modality stream of output data consisting of natural language 765, protein sequence 780, and protein structure 792 modalities. In this particular example, the input query requests a peptide agonist for a specified receptor 705, and the output stream provides a representation of a peptide agonist 796 of that receptor.

In the embodiment exemplified in FIG. 7, the natural language prompt 700 is preprocessed 720 by tokenization and embedding. This results in a set of input tokens. A <start-of-sentence> token 725 indicates that the incoming stream of embedding vectors are of a natural language representation modality.

Similarly, the protein sequence input data 710 is preprocessed 730 by embedding, yielding a set of embedding vectors. A <start-of-sequence> token 735 indicates that the incoming stream is of a protein sequence representation modality.

Similarly, the protein structure input data 715 is preprocessed 740 by embedding, yielding a set of embedding vectors. A <start-of-structure> token 745 indicates that the incoming stream is of a protein structure representation modality.

The set of input vector embeddings are served as input into a mixed modality autoregressive language model 750. A <start-of-sentence> token 755 is used to mark the start of the output stream. The output stream's tokens arise one token per iteration, after which the output is joined with the input context array in standard autoregressive language model fashion. The returned output from one iteration is then available for self attention on the next iteration. In this embodiment, the immediate natural language output of the autoregressive language model is detokenized 760 to yield the natural language.

A <start-of-[MODALITY]> token indicates that the incoming stream will be of the specified modality, as such it serves the dual purpose of indicating that the prior modality will pause (or halt). In this example, the <start-of-sequence> token 770 in the output stream indicates that the natural language modality is paused and the protein sequence modality begins. The output of the protein sequence channel can directly be a protein sequence, and therefore in such embodiments, no post processing 775 involving detokenization and unembedding would be needed. Alternatively, other embodiments can involve a detokenization and unembedding post-processing step 775.

In this embodiment (FIG. 7), the <start-of-structure> token 785 indicates a pause in the protein sequence stream and a start of the protein structure stream. The output stream ends altogether upon encountering an <end-of-output> token 794. Together, the output protein sequence representation 780 and structure representation 792 specify a representation of a peptide agonist 796 of the target receptor 705.

FIG. 8 is an illustrative example of in-context augmentation with retrieved documents in a mixed modality protein and natural language model. The retrieval-augmented input consists of a query 820 as well as the retrieved related documents 800-815. The query and the related documents are each of mixed modality—i.e. consisting of one or more modalities. The insets 890 and 825 illustrate that DOC_K 800 and DOC_0 (Query) 820 each consist of natural language, protein sequence, and protein structure modalities. In particular, the sequence consisting of the concatenation of each of the documents and the query is the combined input and is processed as described in FIG. 7.

FIG. 9 is an illustrative example of a multicapitate encoder-decoder transformer inference architecture for mixed modality protein and natural language fusion. In this embodiment, the encoder 900 can accept a concatenated array of input data of a mix of modalities. In this particular example, the input modalities include natural language (or "text") 904, protein sequence (or "residues") 906, structure inputs 908, and property inputs 910, which are a prespecified data structure (a p-vector) encoding a pre-specified set of properties.

The input data for natural language 904, sequence 906, structure 908, and property 910, are each passed through their respective embeddings, i.e. word embedding 914, residue embedding 916, structure embedding 918, and p-vector embedding 920. The concatenated array of output embedding vectors encodes an input query whose response is a mixed modality output stream at the terminus of the decoder 902. In this particular embodiment, the multicapitate ("multiple headed") architecture consists of one head per output modality: a natural language head 942, a protein sequence head 944, a protein structure head 946, and a small molecule head 948.

Regarding the encoder 900: In this particular embodiment of the invention, each modality of the input data array has a respective embedding. The natural language inputs are first tokenized 912 prior to being passed into its embedding, the word embedding 914. The amino acid sequences are acted on by the respective embedding, the residue embedding 916; the structure inputs are acted on by a structure embedding, and the pre-specified property inputs are acted on by the p-vector embedding. The residue embedding vector is imprinted with a positional encoding 922.

The embedding vector array is then passed into a set of repeating transformer blocks 924. The number of repeats $N_0$ is a design hyperparameter of the architecture. Within each transformer block is a self-attention mechanism. The transformed output array from the encoder is then passed 926 into the decoder for cross-attention.

The encoder 900 can accept a structure input vector 908 into the structure embedding 918. The structure input vector is a vector of structure parameters. In one embodiment, it is of fixed length, L, and zero padding is used for target proteins whose structure parameters are represented by a vector of smaller length than the fixed length, L. The fixed length, L, is a hyperparameter.

The structure embedding 918 is a weight matrix, $W_s$, which the structure input vector, x, 908 multiplies to yield the structure embedding vector, s, as follows:

$$W_s x = s$$

where $W_s$ is an m×L matrix, L is the fixed length of the structure input vector, and m is the length of the amino acid residue embedding vectors, the length of the property (p-vector) embedding vectors, and the length of the word embedding vectors. They all have the same length m. Both m and L are hyperparameters of the model.

The encoder 900 can also accept a protein's amino acid residue inputs 906, which can be in the form of one-hot-encoder vectors which are passed into the residue embedding 916, wherein the residue embedding is itself a trained neural network. A position encoding 922 can be added to the output residue embedding vectors to imprint a signal of sequence position on the respective residue embeddings.

A variable length array of vectors consisting of embedding vector(s)—wherein each vector is from one of the represented modalities—is passed as input into the transformer block 924. The first layer of the transformer block is an attention layer.

Here and in the claims, transformer means a neural network with an attention mechanism. There are a plurality of ways to implement attention mechanisms. In one embodiment, attention layers consist of three types of weight matrices: a query weight matrix, $W_q$, a key weight matrix, $W_k$, and a value weight matrix, $W_v$. Each of the embedding vectors in the array are then multiplied by each of the three matrices to obtain respective queries, keys, and values, as follows:

$$W_q u = q$$

$$W_k u = k$$

$$W_v u = v$$

where u is an embedding vector (i.e. in this embodiment u is a word embedding vector, residue embedding vector, structure embedding vector, or p-vector embedding vector).

For each embedding vector in the array, the dot product of its respective query vector is taken with the key vectors of all token representations in the context array. Next, a softmax operation is done on the resulting array to yield a probability distribution for each token. Next, for each token, a linear combination of values v is taken wherein the coefficient of each value is the respective probability (i.e. attention weight). The output of this linear combination is then taken as the token's respective output into the next layer of the transformer. This is done for each token in the encoder, therefore the length of the input array and the length of the output array from this attention layer are the same. Given the ith token, its corresponding coefficient associated with the jth token can be denoted $C_{ij}$ and is given by, $$c_{ij} = \frac{e^{<qi,kj>}}{\sum_p e^{<qi,kp>}}$$

The attention layer output of the ith token can be denoted $o_i$ and is then given by, $$o_i = \sum_j c_{ij} v_j$$

In some embodiments, the dot product $<q_i, k_j>$ can be scaled by a variance factor.

The array of outputs $o_i$ are then passed into a normalization layer. Furthermore, a copy of the input array which was passed into the attention layer is passed into and added to a normalization layer, skipping the attention layer. This skip connection serves to preserve the pre-attention layer character signal thereby enhancing available signals for inference.

The output from the Add skip & Norm layer is passed into a feed forward neural network layer and from there into another Add skip & Norm layer. The encoder transformer block 924 of "attention→add skip & norm→feed forward→Add skip & norm" is repeated $N_0$ number of times where $N_0$ is a hyperparameter of the model architecture.

Per autoregression, the inputs 928 into the decoder are the right-shifted outputs of the decoder. At each iteration of the autoregression, the input is acted on by the respective embedding 930 to yield an embedding vector which is passed into the set of repeating transformer blocks 936. The transformer blocks of the decoder are as described earlier for the encoder. The current input token and all preceding tokens are visible to the prediction algorithm and furthermore are used as the context array elements for self-attention. The output of the self-attention layer passes into an add-skip-norm layer and onwards into a cross-attention layer. This input is the subject token of the cross-attention layer, while the encoder's final layer output is the remainder of the context array for cross-attention.

The number of repeats $N_1$ of the decoder body transformer block 936 is a design hyperparameter of the model. The resulting final output of the repeating sequence of decoder body transformer blocks is passed 938 into each head of the decoder as shown. In addition, the encoder's final layer output is also passed 940 into each of the decoder's heads for cross-attention.

The respective number of repeats—$N_2$, $N_3$, $N_4$, $N_5$—of the decoder head transformer blocks are also design hyperparameters of the model. Furthermore, they can be zero, in that some heads may have no transformer blocks.

The final output layer of the decoder head transformer blocks is passed into a linear layer which spans the possible values of each respective head. E.g. in the case of the natural language head it spans the language's vocabulary; in the case of the sequence head, it spans the set of amino acids; in the case of small molecule drug (SMD) head, it spans a library of SMDs. In each case the domain also includes auxiliary tokens such as <start-of-[MODALITY]> tokens or <end-of output> tokens.

The linear layer output in turn passes into a softmax layer, yielding a probability distribution over the possible values of the respective heads including auxiliary tokens such as <start-of-[MODALITY]> tokens or <end-of output> tokens. The output probability distribution is then sampled to yield the output token at each iteration of the autoregression.

Ones with ordinary skill in the art will recognize that the invention disclosed herein can be implemented over an arbitrary range of computing configurations. We will refer to any instantiation of these computing configurations as the computing environment. An illustrative example of a computing environment is depicted in The Computing Environment FIG. Examples of computing environments include but are not limited to desktop computers, laptop computers, tablet personal computers, mainframes, mobile smart phones, smart television, programmable hand-held devices and consumer products, distributed computing infrastructures over a network, cloud computing environments, or any assembly of computing components such as memory and processing—for example.

As illustrated in The Computing Environment FIG, the invention disclosed herein can be implemented over a system that contains a device or unit for processing the instructions of the invention. This processing unit 16000 can be a single core central processing unit (CPU), multiple core CPU, graphics processing unit (GPU), multiplexed or multiply-connected GPU system, or any other homogeneous or heterogeneous distributed network of processors.

In some embodiment of the invention disclosed herein, the computing environment can contain a memory mechanism to store computer-readable media. By way of example and not limitation, this can include removable or non-removable media, volatile or non-volatile media. By way of example and not limitation, removable media can be in the form of flash memory card, USB drives, compact discs (CD), blu-ray discs, digital versatile disc (DVD) or other removable optical storage forms, floppy discs, magnetic tapes, magnetic cassettes, and external hard disc drives. By way of example but not limitation, non-removable media can be in the form of magnetic drives, random access memory (RAM), read-only memory (ROM) and any other memory media fixed to the computer.

As depicted in The Computing Environment FIG, the computing environment can include a system memory 16030 which can be volatile memory such as random access memory (RAM) and may also include non-volatile memory such as read-only memory (ROM). Additionally, there typically is some mass storage device 16040 associated with the computing environment, which can take the form of hard disc drive (HDD), solid state drive, or CD, CD-ROM, blu-ray disc or other optical media storage device. In some other embodiments of the invention the system can be connected to remote data 16240.

The computer readable content stored on the various memory devices can include an operating system, computer codes, and other applications 16050. By way of example not limitation, the operating system can be any number of proprietary software such as Microsoft windows, Android, Macintosh operating system, iphone operating system (IOS), or Linux commercial distributions. It can also be open source software such as Linux versions e.g. Ubuntu. In other embodiments of the invention, data processing software and connection instructions to a sensor device 16060 can also be stored on the memory mechanism. The procedural algorithm set forth in the disclosure herein can be stored on—but not limited to—any of the aforementioned memory mechanisms. In particular, computer readable instructions for training and subsequent image classification tasks can be stored on the memory mechanism.

The computing environment typically includes a system bus 16010 through which the various computing components are connected and communicate with each other. The system bus 16010 can consist of a memory bus, an address bus, and a control bus. Furthermore, it can be implemented via a number of architectures including but not limited to Industry Standard Architecture (ISA) bus, Extended ISA (EISA) bus, Universal Serial Bus (USB), microchannel bus, peripheral component interconnect (PCI) bus, PCI-Express bus, Video Electronics Standard Association (VESA) local bus, Small Computer System Interface (SCSI) bus, and Accelerated Graphics Port (AGP) bus. The bus system can take the form of wired or wireless channels, and all components of the computer can be located remote from each other and connected via the bus system. By way of example and not of limitation, the processing unit 16000, memory 16020, input devices 16120, output devices 16150 can all be connected via the bus system. In the representation depicted in The Computing Environment FIG, by way of example not limitation, the processing unit 16000 can be connected to the main system bus 16010 via a bus route connection 16100; the memory 16020 can be connected via a bus route 16110; the output adapter 16170 can be connected via a bus route 16180; the input adapter 16140 can be connected via a bus route 16190; the network adapter 16260 can be connected via a bus route 16200; the remote data store 16240 can be connected via a bus route 16230; and the cloud infrastructure can be connected to the main system bus vis a bus route 16220.

In some embodiment of the invention disclosed herein, The Computing Environment FIG illustrates that instructions and commands can be input by the user using any number of input devices 16120. The input device 16120 can be connected to an input adapter 16140 via an interface 16130 and/or via coupling to a tributary of the bus system 16010. Examples of input devices 16120 include but are by no means limited to keyboards, mouse devices, stylus pens, touchscreen mechanisms and other tactile systems, microphones, joysticks, infrared (IR) remote control systems, optical perception systems, body suits and other motion detectors. In addition to the bus system 16010, examples of interfaces through which the input device 16120 can be connected include but are by no means limited to USB ports, IR interface, IEEE 802.15.1 short wavelength UHF radio wave system (bluetooth), parallel ports, game ports, and IEEE 1394 serial ports such as FireWire, i.LINK, and Lynx.

In some embodiment of the invention disclosed herein, The Computing Environment FIG illustrates that output data, instructions, and other media can be output via any number of output devices 16150. The output device 16150 can be connected to an output adapter 16170 via an interface 16160 and/or via coupling to a tributary of the bus system 16010. Examples of output devices 16150 include but are by no means limited to computer monitors, printers, speakers, vibration systems, and direct write of computer-readable instructions to memory devices and mechanisms. Such memory devices and mechanisms can include by way of example and not limitation, removable or non-removable media, volatile or non-volatile media. By way of example and not limitation, removable media can be in the form of flash memory card, USB drives, compact discs (CD), blu-ray discs, digital versatile disc (DVD) or other removable optical storage forms, floppy discs, magnetic tapes, magnetic cassettes, and external hard disc drives. By way of example but not limitation, non-removable media can be in the form of magnetic drives, random access memory (RAM), read-only memory (ROM) and any other memory media fixed to the computer. In addition to the bus system 16010, examples of interfaces through which the output device 16150 can be connected include but are by no means limited to USB ports, IR interface, IEEE 802.15.1 short wavelength UHF radio wave system (bluetooth), parallel ports, game ports, and IEEE 1394 serial ports such as FireWire, I.LINK, and Lynx.

In some embodiment of the invention disclosed herein some of the computing components can be located remotely and connected to via a wired or wireless network. By way of example and not limitation, The Computing Environment FIG shows a cloud 16210 and a remote data source 16240 connected to the main system bus 16010 via bus routes 16220 and 16230 respectively. The cloud computing infra- structure 16210 can itself contain any number of computing components or a complete computing environment in the form of a virtual machine (VM). The remote data source 16240 can be connected via a network to any number of external sources such as NMR spectrometry devices, X-ray diffraction devices, electron microscopes, imaging devices, imaging systems, or imaging software.

In some embodiment of the invention disclosed herein, a sensor system 16060 which captures and pre-processes data is attached directly to the system. For example, this may be an electron microscope (and associated image processing software); it may be a camera in the case of an imaging system, say for processing distance map photographs; or it may be an X-ray crystallography machine or an NMR spectrometer (and associated software), etcetera. Stored in the memory mechanism—16020, 16240, or 16210—are machine learning models, algorithms, and data products developed according to the procedures set-forth herein. Computer-readable instructions are also stored in the memory mechanism, so that upon command, protein struc- ture representation data, its substrates and associated data can be captured or can be received over a network from a remote or local previously collated database. This transmis- sion of data can be done over a wired or wireless network as previously detailed, as the source and/or recipient of the data output can be at a remote location.

The objects set forth in the preceding are presented in an illustrative manner for reason of efficiency. It is hereby noted that the above disclosed methods and systems can be imple- mented in manners such that modifications are made to the particular illustration presented above, while yet the spirit and scope of the invention is retained. The interpretation of the above disclosure is to contain such modifications, and is not to be limited to the particular illustrative examples and associated drawings set-forth herein.

Furthermore, by intention, the following claims encom- pass all of the general and specific attributes of the invention described herein; and encompass all possible expressions of the scope of the invention, which can be interpreted—as pertaining to language—as falling between the aforemen- tioned general and specific ends.

What is claimed:

1. A method, comprising:
   a) receiving, at a processor, a trained mixed modality neural network:
      i) wherein representation modalities are for represen- tations of features of proteins,
      ii) wherein the represented features include one or more of sequence, structure, function, interactions, inter- actors, binding partners, attributes, and properties,
      iii) wherein the respective modalities of the represen- tations include:
         (1) natural language representation modality, and
         (2) sequence representation modality,
      iv) wherein the neural network is configured to accept as input data, a query consisting of one or more of the modalities, and to yield as output data, a response to the query, wherein the response also consists of one or more of the modalities;
   b) receiving, at a processor, a retriever function:
      i) wherein the retriever is configured to accept as input, queries to the mixed modality neural network, ii) wherein given as input, a query to the mixed modality neural network, the retriever function's output includes a set of documents related to the input query;
   c) using the trained mixed modality neural network to obtain a representation of a protein as output:
      i) wherein the output is obtained in response to a combined input of the input query and the set of related documents;
   d) synthesizing the protein.

2. The method of claim 1, wherein the biological activity of the protein is tested in vitro or in vivo.

3. The method of claim 1, wherein retriever function is a neural network trained on a similarity objective.

4. The method of claim 1, wherein the trained mixed modality neural network is an autoregressive transformer.

5. The method of claim 4, wherein for each respective head of the transformer, final output is a probability distri- bution over a set of possible values at that head.

6. The method of claim 5, wherein the input query specifies a target receptor and requests a peptide ligand of the receptor; and wherein the output is a representation of a peptide ligand of the specified target receptor.

7. The method of claim 6, for generating a representation of a peptide ligand of a target receptor, wherein the method is also for generating and synthesizing an effective peptide ligand, the method further comprising:
   a) generating the output by randomly sampling the output probability distribution of the active head, at each iteration of the autoregression;
   b) using the same input query, repeating the random- sampling based generation process a plurality of times, each yielding a candidate peptide ligand;
   c) assessing the interaction, efficacy, and properties of each candidate ligand with the target receptor;
   d) selecting the most effective ligand;
   e) synthesizing the ligand.

8. The method of claim 7, wherein for each of the modalities on this list: (a) natural language, (b) protein sequence, and (c) protein structure; the input embedding used for input data of the respective modality is distinct from the input embedding used for input data of any of the other modalities on the list.

9. A method comprising
   a) receiving a trained mixed modality neural network:
      i) wherein the representation modalities are for repre- sentations of features of proteins,
      ii) wherein the represented features include one or more of sequence, structure, function, interactions, inter- actors, binding partners, attributes, and properties,
      iii) wherein the respective modalities of the represen- tations include:
         (1) natural language representation modality,
         (2) sequence representation modality,
         (3) structure representation modality, and
         (4) small molecule drug representation modality,
      iv) wherein the neural network is configured to accept as input data, a query consisting of one or more of the modalities, and to yield as output data, a response to the query, wherein the response also consists of one or more of the modalities,
      v) wherein the neural network has multiple output heads, each with its own loss function,
      vi) wherein the neural network heads include one head for natural language representation output, a differ- ent head for protein sequence representation output, a different head for protein structure representation output, and a different head for small molecule drug representation output;

b) receiving a retriever function:

i) wherein the retriever is configured to accept as input, queries to the mixed modality neural network, ii) wherein given as input, a query to the mixed modality neural network, the retriever function's output includes a set of documents related to the input query;

c) using the trained mixed modality neural network to obtain a representation of a ligand as output:

i) wherein the output is obtained in response to a combined input of the input query and the set of related documents;

d) manufacturing the ligand.

10. The method of claim 9, further comprising testing the biological activity of the ligand in vitro or in vivo.

11. The method of claim 10, wherein the input query specifies a target receptor and requests a peptide ligand of the receptor; and wherein the manufactured ligand is a peptide.

\* \* \* \* \*